United States Patent [19]
Aroutiounian et al.

[11] Patent Number: 5,382,341
[45] Date of Patent: Jan. 17, 1995

[54] METHOD OF MAKING SMOKE DETECTOR

[76] Inventors: Vladimir M. Aroutiounian, 17 Nalbandian Street, Apt. 18, Yerevan 375010; Zaven N. Adamian, 6 Orbeli Street, Flat No. 34, Yerevan 375028; Hrachia V. Abovian, 3 Halabian Street, Flat No. 28, Yerevan 375038; Kurgin R. Movsessian, Buracan, Ashtarak Ds. 378400; Ara A. Barsegyan, 151/1 Kamo Street, Flat No. 32, Yerevan 375094; Manuk S. Panossian, Nubarashen Avan 15th Street No. 3, Yerevan 375071, all of Armenia

[21] Appl. No.: 943,071

[22] Filed: Sep. 10, 1992

[51] Int. Cl.⁶ .............. C23C 14/30; C23C 14/08; C23C 14/34
[52] U.S. Cl. .............. 204/192.21; 73/31.06; 338/34; 427/101; 427/255; 427/374.1; 422/95; 422/97; 29/620
[58] Field of Search ............ 204/192.21; 427/101, 427/255, 374.1; 338/34; 422/95–97; 73/31.06; 29/620

[56] References Cited

U.S. PATENT DOCUMENTS

| | | | |
|---|---|---|---|
| 3,900,815 | 8/1975 | Taguchi | 338/34 |
| 4,016,524 | 4/1977 | Pompei et al. | 338/34 |
| 4,307,373 | 12/1981 | Johnston | 338/34 |
| 4,313,338 | 2/1982 | Abe et al. | 73/23 |
| 4,338,281 | 7/1982 | Treitinger et al. | 422/98 |
| 4,343,768 | 8/1982 | Kimura | 422/97 |
| 4,579,751 | 4/1986 | Forster | 427/595 |
| 4,640,628 | 2/1987 | Seki et al. | 374/141 |
| 4,911,892 | 3/1990 | Grace et al. | 422/94 |
| 4,928,513 | 5/1990 | Sugihara et al. | 73/1 G |
| 5,051,718 | 9/1991 | Satake et al. | 338/34 |

*Primary Examiner*—Aaron Weisstuch
*Attorney, Agent, or Firm*—Michael I. Chakansky

[57] ABSTRACT

This invention relates to solid-state smoke detectors and smoke (fire) alarm systems, and more particularly to a novel and improved smoke-sensitive element comprising a bismuth oxide film deposited on one surface of an electrically insulating material. It also relates to a method of depositing this oxide on a substrate, of heat treatment which provides for a highly smoke-sensitive film, and to smoke detector signal processing circuits.

18 Claims, 5 Drawing Sheets

METHOD OF MAKING SMOKE DETECTOR

BACKGROUND OF THE INVENTION

This invention relates to solid-state smoke detectors and smoke (fire) alarm systems, and more particularly to a novel and improved smoke-sensitive element comprising a bismuth oxide film deposited such as by electron beam evaporation, sputtering, or otherwise, by means well known in the art, on one surface of an electrically insulating material and a pair of electrodes. It also relates to a method of depositing this oxide on a substrate and of heat treatment which provides for a highly smoke-sensitive film which does not require additional heating elements during operation. This invention also relates to smoke detector signal processing circuits.

A small, inexpensive smoke detector capable of operating with high sensitivity, quick response, extremely low power consumption, high accuracy, and reliability is desirable. Prior art detectors have used heating to ensure the desired sensitivity of the detector element. However, heating the element consumes a significant amount of power and can lead to instability in some of the sensitivity characteristics of the smoke detecting element.

Many smoke detectors operate upon the principle that an ionization current catalyzed by a radiation source is affected by the presence of particulates such as those found in aerosols or smoke emanating from a fire. The particulates change the ionization current and the change in current can be detected and correlated with the density of the particulate matter to provide a fairly accurate indication of a smoke condition.

A radioactive source placed in an ionization chamber can be used as the radiation source, as disclosed for example in U.S. Pat. No. 4,037,206 and as discussed in the book "Fire Safety, Explosion Safety" edited by Baratov (1987). Such ionization smoke detectors are currently produced by industry and can be powered with a battery. However, it is necessary to be very careful with such smoke detectors in living accommodations, hotels and so on.

Optical smoke detectors utilize the change in air transparency due to the existence of smoke to detect smoke. The light for an optical smoke detector may be provided for example by a tungsten lamp or a light-emitting diode (LED) and the light sensor may be a photosensitive semiconductor device. For examples of optical smoke detectors see Baratov (1987). However, optical smoke detectors are complicated and may contain many different electronic components. Additionally, precautions must be taken to minimize the chance of a false alarm, since a false alarm may be triggered by a false light signal from the sun, a lamp or some other extraneous source of light or even a change of air transparency caused by dust.

Different types of metal-oxide semiconducting gas sensors are well known. There are numerous kinds of gas sensing elements, for example, thin-film, thick-film, sintered and ceramic. In order to enable the gas sensing elements to effectively detect a gas it is usually necessary to heat the element in operation in order to increase its sensitivity to a useful level. There are several methods for heating the sensitive element and for fabricating the sensitive element, reference sensor unit and heater. In some cases a catalytic layer or catalytic islands are deposited on the substrate to enhance sensitivity. The details of such gas sensing elements are discussed in many publications, for example, Aroutiounian (1991) and U.S. Pat. Nos. 4,338,281, 4,343,768, 4,574,264, 4,580,439, 4,911,892 and 4,928,513.

The following two patents, U.S. Pat. Nos. 3,900,815 and 4,016,524 disclose, for example, semiconductive elements for smoke detectors. In accordance with these patents, the semiconductor is covered with a dielectric film formed with a large number of microscopic openings or pores. In Nitta & Terada (1982) the authors disclose a porous p-type semiconductive $MgCr_2O_4TiO_2$ ceramic as the gas-sensitive material. Its electrical conductivity changes with different gas chemisorption. Sensitivity of such a ceramic to smoke is remarkably small compared to its sensitivity to $H_2S$ and various organic molecules containing functional radicals ($CH_3CHO$, $C_2H_5OH$, etc.) in the range of heating temperatures up to 550° C. Another multifunctional (smoke and different gases) detector with heater and catalyst metal layer is disclosed in U.S. Pat. No. 4,569,826.

One problem with prior art detectors is that they can be sensitive to a large number of different gases and limiting the sensitivity can be a complex process. As is disclosed in the above mentioned publications, the same metal-oxide body with different catalyst metal layer or doping, together with a multilayer film can be used for detecting a number of different gases; in the case of $SnO_2$, the number of gases detected can reach more than 20. To provide for selectivity of the detector it is necessary to change the heating temperature and dope the semiconductor body with different impurities or oxides. Regretfully, even today, there are problems with the selectivity of semiconductor detector and the rather high electric power consumption in the waiting mode or idle, non-alarm, state during the detector's operation.

Researchers have investigated different bismuth-containing materials. Influence of the dielectric $Bi_2O_3$ thin layer on properties of semiconductive metal-oxide-GaAs solar cells is discussed in Wang & Pandeliser (1981) and Pandeliser & Wang (1982). There are other $Bi_2O_3$ applications, but bismuth-containing materials are rarely used for the purpose of gas detector fabrication. The complex oxide, bismuth molybdenum oxide is disclosed in U.S. Pat. No. 4,307,373 as having an electrical conductivity dependent on the presence and/or concentration of a gas or gases in the ambient atmosphere. Bismuth ferrites $BiFeO_3$, $Bi_4Fe_2O_9$ and $Bi_2Fe_2O_9$, as well as, $Bi_4V_2O_{11}$ are disclosed as being useful as sensitive compounds for detecting acetone, ethanol or gasoline vapors and natural gas in USSR Patent No. 1,569,689 and in Pogossian & Abovian (1991). As disclosed in Hykaway & Sears (1988), bismuth molybdate evaporated films are sensitive to alcohols, ketones, alkenes, hydrogen, carbon monoxide and water vapors. However, the operating temperature of the prior art bismuth containing gas sensitive compounds was much higher than the room temperature.

The possibility of using ultrafine particles of a metal oxide as a gas sensitive material where the oxide of Bi or seventeen other metals may be made is disclosed in U.S. Pat. No. 4,313,338 ("the '338 patent"). The '338 patent focused on detectors based on $SnO_x$ and $CuO_x$ which detected isobutane and ethyl alcohol and also could be used as humidity sensors. However, it was necessary to heat the disclosed sensitive films to at least above 100° C. (see, for example, FIGS. 4, 10, 12 and 13, the '338 patent). In addition, the oxide had to be cerated by a special method in oxygen gas plasma (see, for example, FIGS. 11, 14, 15, the '338 patent) with ultrafine particles having a mean diameter of between ten and several hundred angstroms. These particles should be small monocrystals of a mixture of appropriate metals (Sn or Cu) with its oxides (SnO, $SnO_2$ or CuO, $Cu_2O$). After preparing such a gas-sensitive film of ultrafine particles ($SnO_2$—SnO—Sn, for example) in a boat in one part of the evaporator in an oxygen atmosphere while in the other boat in the same evaporator an extra thin film of ultrafine particles of palladium having a mean particle diameter of several ten angstroms and having a thickness of about 2 to 5 millimeters was deposited in an inert gas medium. It was also disclosed that in obtaining measurements of sensor characteristics an alternating current power source was used.

Besides listing bismuth, the '338 patent does not disclose any information about bismuth, or the other fifteen oxides, nor does it disclose any information about sensitivity to smoke or other gases. The '338 patent discloses the use of a heating means and an aggregate of ultrafine Sn or Cu particle oxides and palladium. Moreover, the '338 patent, and the other above mentioned patents all disclose heating the sensitive film body in operation and most of them disclose the necessity of coating the sensitive film layer with islands or particles of catalyst metal or their oxides.

UK Patent No. GB2043913A discloses a gas-sensitive element whose electrical resistance at room temperature is dependent upon the concentration of a reducing gas to which it is exposed. It comprises of a major proportion of indium oxide and a minor proportion (2 to 12.5%) of platinum black. It is made by grinding a mixture of indium oxide or an indium salt decomposible to it and platinum black or a platinum compound decomposible to it, baking and sintering. This patent does not disclose the sensitivity of this material to smoke, nor does it eliminate the general deficiency of the prior art devices of requiring the use of noble and expensive metals such as platinum or palladium.

Signal processing circuits diagrams for sensors are well known (see, for example, Chorwitz and Hill and UK Patent No. GB2043913). The sensor (and the smoke-sensitive element in particular) connects usually in a bridge circuit which gets out of balance when the smoke appears in the air atmosphere. Such circuits are complicated, have low sensitivity and noise immunity, and consume rather large amounts of electrical power in the waiting mode.

The prior art does not teach that a resistive film of bismuth oxide can operate without heating as the sensing material for a smoke (fire) detector. The prior art does not teach depositing bismuth oxide on an electrically insulating substrate as a resistive film and supplying a pair of electrodes so as to provide a smoke (fire) sensitive element and/or device. The prior art does not teach the regimes of deposition and heat treatment for fabrication of the necessary modification of bismuth oxide as taught in the present invention, as well as signal processing circuits which are necessary for reliable and effective operation of a smoke detector based on this particular sensitive element.

SUMMARY OF THE INVENTION

It is an object of the present invention to provide a smoke sensitive element and an appropriate smoke detector having high sensitivity, extremely low power consumption and dissipation in the waiting mode of operation of sensor, and fast response.

We chose bismuth sesquioxide $Bi_2O_3$ as our preferred smoke sensitive material based on our research with simple and complex bismuth oxides as disclosed in Pogossian (1991) and in USSR Patent No. 1,569,669. It was known from publications that there are many modifications of $Bi_2O_3$. Varying of bismuth ions valency allows easy fabrication of different type of oxides ($Bi_2O$, BiO, $Bi_2O_{2.7-2.8}$, $Bi_2O_3$, $Bi_2O_4$, $Bi_3O_5$, $Bi_2O_5$) with different stabilities and a wide range of specific resistance values. Through our X-ray phase diagram testing and analysis we established that we were dealing with $Bi_2O_3$ oxide and that after heat treatment the metallic phase of Bi disappeared.

Bismuth sesquioxide $Bi_2O_3$ has five modifications ($\alpha$, $\sigma$, $\beta$, $\gamma$, and $\delta$) and does not dissolve in water and, for most purposes, in alkalines. This oxide is stable in water and other gas vapors medium. For use as a smoke detecting sensor, it is necessary to get rid of the metallic phase of Bi, in the thin film of $Bi_2O_3$ made in accordance with the present invention, by different deposition methods, by use of a corresponding heat treatment which is discussed below. This modified $Bi_2O_3$ made in accordance with the present invention is referred to hereinafter as "bismuth oxide (deposited and heat treated)".

Smoke in the air is understood as a rather complicated gas-aerosol medium formed as the result of combustion (fire). The composition of smoke is very complicated and depends on the resulting products of the combustion (see, for example, Baratov (1987)). Therefore, smoke is generally not a simple one pure gas phase, but may have many types of combustion products which affect the active resistance of the sensitive material.

In accordance with the present invention, sensitivity to smoke (fire) is provided by use of bismuth oxide (deposited and heat treated) as the sensitive element material. This material is formed as a resistive film on an electrically insulating substrate upon which is located a pair of electrodes or other means for electrically connecting the sensitive element material to any device or material which can measure changes in resistance. In another embodiment, the pair of electrodes can be made directly on the bismuth oxide (deposited and heat treated).

Other objects, features and advantages of the present invention will be apparent from the following detailed description of preferred embodiments thereof taken in conjunction with the accompanying drawings.

DESCRIPTION OF THE PREFERRED EMBODIMENTS

Figure 1A:
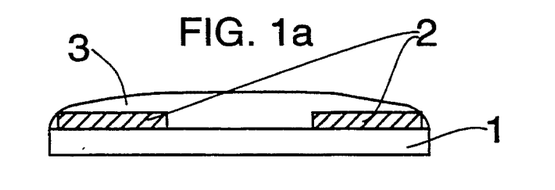
FIGS. 1a and 1b, respectively, show the smoke sensitive elements in schematic sectional and plane views.
Figure 1B:
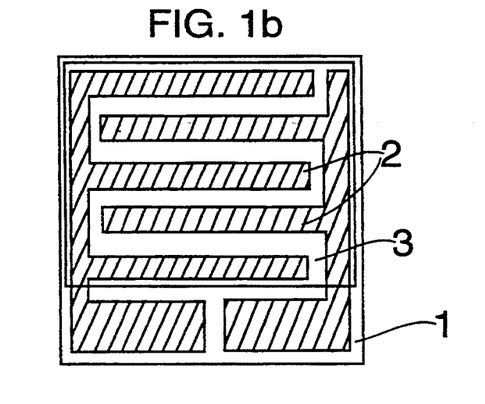

The structure of one embodiment of the smoke sensitive element of the present invention will now be described with reference to the figures. FIGS. 1a and 1b show the electrically insulating substrate such as glass, a glass ceramic (sytall), a sapphire, dielectric ceramics, a synthetic resin, or other material with very high electric specific resistance. For example, films of silicon dioxide ($SiO_2$) silicon nitride ($Si_3N_4$), alund ($Al_2O_3$) and most, if not all, other electrically insulating coating materials usually used in modern microelectronics for insulation of active parts (insulated islands) in semiconductor devices and integrated circuits made on a base of Si, GaAs, InP and other materials and alloys may be used as the insulating substrate.

A pair of electrodes 2 are deposited or otherwise placed in electrical contact with one of the major substrate surfaces 1 forming interdigital contacts. Each of these comb-shaped electrodes may be a thin metal film (nickel, aluminum, gold or other material) in the form of strips or combs, or may be a thin film of high conducting metal oxide, which can be formed by silk screening an ink or paste containing the metal oxide. A resistive film 3 formed of bismuth oxide SHT is prepared in accordance with the present invention as set forth below.

Electrodes may be attached to the substrate by any of the well known methods, it is only necessary to provide reliable adhesion and a low specific resistance of contacts, that is good electrical connectivity. Electrodes may be attached under (see FIGS. 1a and 1b) or on the sensitive film of bismuth oxide (deposited on heat treated). Electrodes can be supplied with flexible leads to connect the sensitive element to the signal processing circuit.

The number of teeth of the electrodes 2 may be varied to provide the necessary resistance value of smoke-sensitive film 3. Electrodes 2 are connected to an external circuit which can reside separately on another substrate or on the same active or passive substrate (in the case of integrated circuits on the base of smoke-sensitive element of the present invention). The comb-shaped electrode pattern is illustrated in FIGS. 1a and 1b by way of example only. In the case of one active substrate embodiment, the electronic components of integral processing and alarm microcircuit are formed in the body of the semiconductive substrate (silicon, GaAs, InP, etc.). A passive substrate may be used for preparing hybrid microcircuits and constitute an electrically insulating layer or plate.

In accordance with the present invention, the smoke-sensitive film 3 should preferably be prepared as follows. The dimensions of the smoke sensitive element are not restricted, since the sensitivity does not depend on the dimensions but is determined by the quality of the smoke-sensitive film, which in turn is determined by its surface properties, heat treatment, and deposition regimes. The film 3 may be a multilayer film including a combination of the bismuth oxide (deposited and heat treated) and different sublayers necessary for good adhesion with the substrate. However, the surface of film 3 which will be in contact with the smoke should be deposited with a bismuth oxide layer made in accordance with the present invention.

While we discuss the technology of electron beam evaporation of $Bi_2O_3$, of course, there are no principal limitations on the manner for preparing bismuth sesquioxide thin film which in accordance with the present invention could be made by any well-known method of deposition, including evaporation, sputtering, vacuum deposition, electrolytic deposition, cathode deposition, or other methods. To deposit the bismuth oxide film using electron beam evaporation, the material to be evaporated should be in the form of powder or a pressed tablet and placed into a crucible, and the chamber pumped out down to a pressure (P) of about $1 \times 10^{-3}$ pascal (Pa).

Next an electron-beam evaporator is introduced into the required mode, the beam power ranging from 0.25 to 0.4 kilowatts (kW); and the resulting evaporation rate being from 500 to 1000 angstroms (Å) per minute. Increasing the power of the electron-beam evaporator above this level leads to active splashing and melting of the material in the crucible. Despite this fact, no interaction between the tungsten crucible and evaporated material was observed, but the material color was observed to change from yellow to grey-blue or black. The bismuth oxide film was deposited at the substrate temperature of about 420 to 470 degrees kelvin (°K.), about 147°–197° C., thus providing the necessary adhesion to the glass ceramic (sytall).

Specific resistance of the bismuth oxide film strongly depends on the evaporation rate and very weakly on the oxygen pressure in the chamber ($P = 5 \times 10^{-3}$ Pa $-1 \times 10^{-2}$ Pa).

The greatest specific resistance of about $10^5$ ohm-centimeters was characteristic of the bismuth oxide films obtained at a low evaporation rate of about 500 Å per minute. Decrease of the film's specific resistance at evaporation rates greater than 500 Å per minute may be connected with the bismuth sesquioxide molecular dissociation:

That is, in the course of evaporation, the bismuth oxide molecule releases oxygen which is removed by the pumping system and the deposited film contains metal bismuth. Its presence may be verified by X-ray phase analysis. The bismuth oxide film obtained in this way is not generally sensitive to smoke.

To replenish the oxygen deficiency, the film is heat-treated in the air. When the temperature is increased at about 180°–240° C. per minute to a temperature of 460°–750° C. (733°–1023° K.) the specific resistance also rises and can achieve a value of about $3 \times 10^7$ ohm-centimeters.

A preferred temperature range is determined by the presence of the metal bismuth in the film as established by testing the film's specific resistance, e.g., by plotting resistance as a function of temperature and X-ray measurements, thus accounting for the film's metallic type conductivity. A temperature increase above about 500° K. (227° C.) appears to cause the specific resistance to start to decrease. In the range from about 500° K. (227° C.) to 800° K. (727° C.) the oxygen deficiency in the film gradually decreases, and at the temperature of about 800° K. (1073° C.) metal bismuth disappears completely. In the range of temperature of about 800° K. (527° C.) to 1000° K. (727° C.) ordering of the crystalline structure is observed.

A preferred temperature range for maximal sensitivity to smoke of the bismuth oxide film of the present invention is about 670°–730° C. (943°–1003° K.). The film should be held at this temperature range for about 10–20 seconds, and then cooled at the rate of about 180°–240° C. per minute. Cooling the bismuth oxide film in this manner leads to the increase in the film's specific resistance, and such increase may be observed up to room temperature. The sharp increase in resistance of the heat-treated film in comparison to the initial value of the non-heat-treated material indicates that the oxidation process of metal bismuth in the film deposited by electron beam evaporation, which is then heat treated, is irreversible.

Besides the resistance change, the film color also altered, ranging from grey to black depending on the evaporation rate and substrate temperature. In the range from 700° to 800° K., the films grew transparent with shades depending on the thickness. At temperatures above 1000° K. the films grew white.

Figure 2:
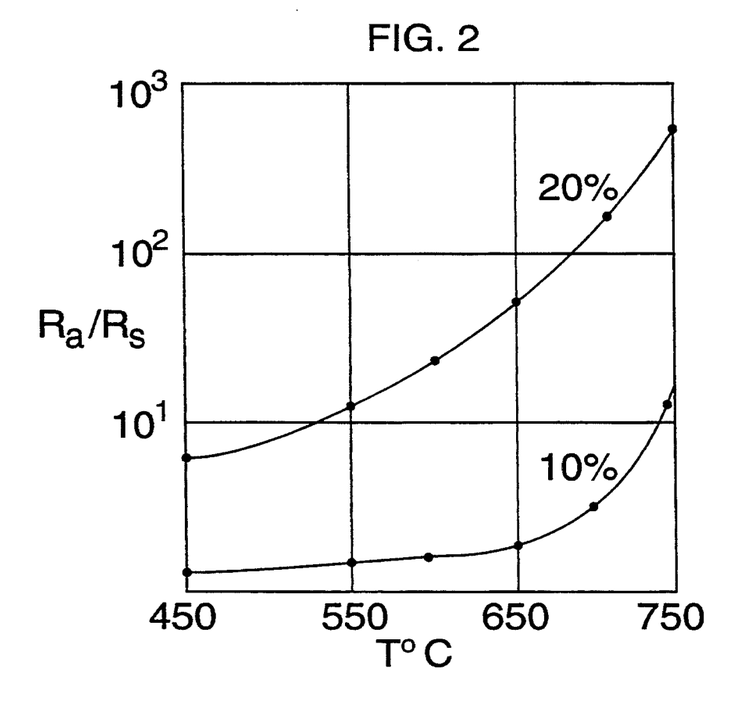
FIG. 2 shows the ratio of the resistance $R_a$ in air in the absence of smoke at the smoke sensitive layer of the present invention to its resistance $R_s$ in the presence of smoke as a function of the heat treatment temperature in degrees celsius (°C.).

The heat-treated film of bismuth oxide thus obtained is highly sensitive to the smoke, the sensitivity increasing with the rise of heat treatment temperature, but the temperature of heat treatment is optimal in the range of temperatures of about 943° to 1003° K. (670° to 730° C.), as shown in FIG. 2.

When depositing a pair of electrodes on the smoke sensitive bismuth oxide (deposited and heat treated), the temperature of the film and the substrate should not exceed 300° C. (573° K.). A sensitive film of bismuth oxide may also be obtained by application of other techniques, such as magnetron sputtering, thermal, ionic deposition and other methods known in the art, when used together with the heat treatment of the present invention.

The smoke-sensitive element of the present invention is capable of providing useful operation without the necessity of heating the base of the substrate or sensitive film, and without the deposition on the surface of the film of catalytic metal in form of islands, particles and/or superthin film. Nevertheless, the sensor of the present invention does not lose sensitivity to smoke if the base is heated or catalytic material deposited upon it.

The smoke-sensitive elements and detectors of the present invention are highly resistant to electronic jamming, small, light in weight, consume less power in the waiting mode of operation, and are economical, when compared to the detectors of the prior art.

The smoke-sensitive elements of the present invention may be fabricated together with hybrid and fully integrated smoke-sensitive microcircuits, in which case one part of the element can be the smoke-sensitive element, and the other the signal processing and alarm circuits.

FIG. 2 shows the dependence of the resistance of a smoke-sensitive element made in accordance with the present invention and fabricated on the base of the bismuth oxide by the above-mentioned method of heat treatment (temperature T is given in °C.). $R_a$ is the resistance of the smoke detecting element in air in the absence of smoke and $R_s$ is the resistance in the presence of smoke in the air. The lower curve corresponds to the case of 10% content of smoke in air, the upper curve corresponds to a 20% smoke content. In the latter case, 20% smoke content, $R_s$ can be decreased to less than a thousandth of its nonoptional heat-treated resistance.

Figure 3:
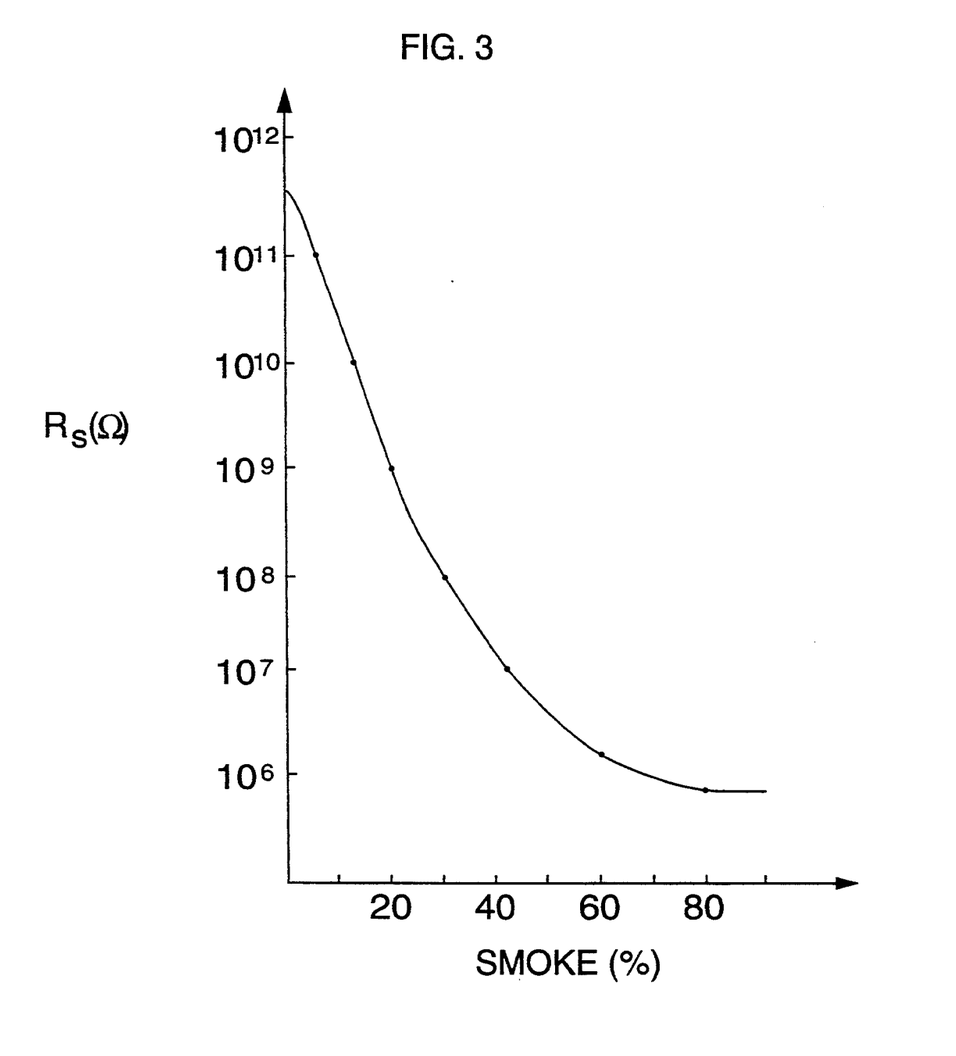
FIG. 3 shows typical dependence of the resistance of the smoke sensitive layer of the present invention as a function of the concentration of the smoke in the air in percent (%).

FIG. 3 shows typical dependence of the resistance of a smoke-sensitive element of the present invention upon concentration of the smoke in the air. The smoke-sensitive element's resistance $R_s$ is measured, as is usually the case, in a series connection with a reference resistor. The ratio of the detector resistance $R_a$, in the air without smoke, to its resistance $R_s$, in the smoky medium (atmosphere), gives a value of the sensitivity of the smoke-detector.

Figure 4:
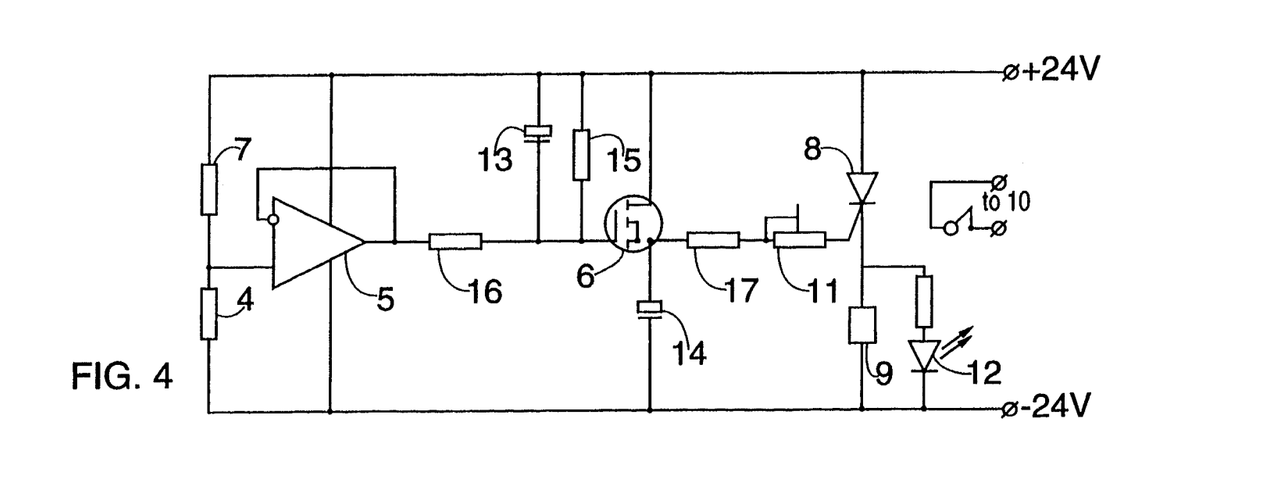
FIGS. 4 to 6 show signal processing circuit diagrams of the smoke detector for one preferred embodiment of the present invention.
Figure 5:
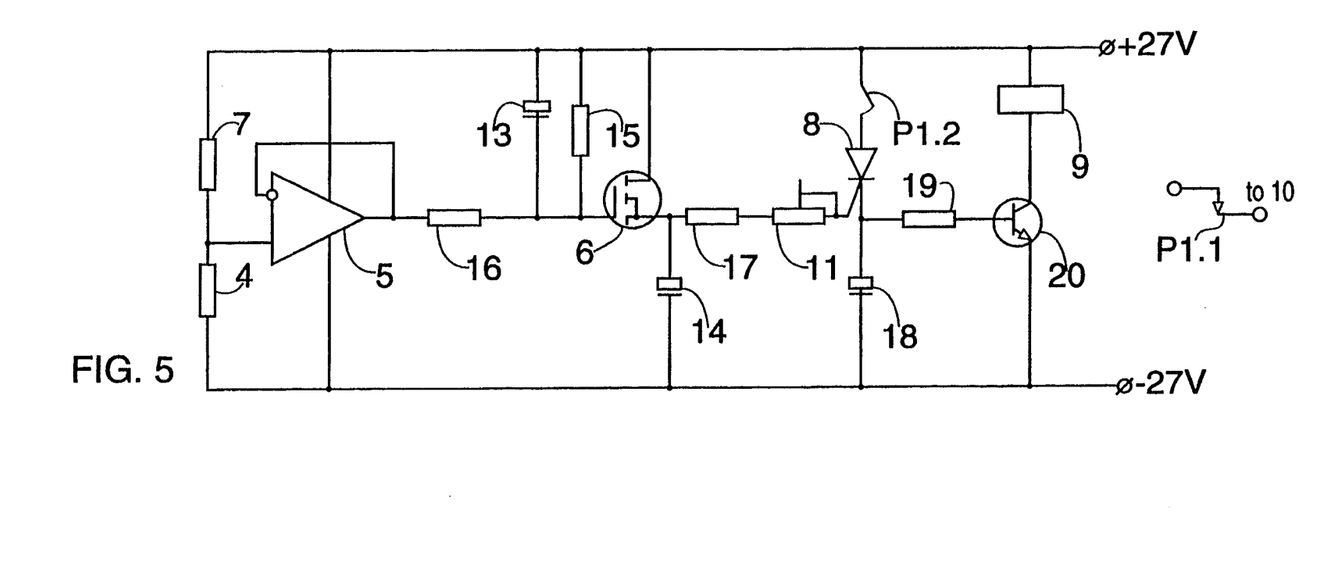
Figure 6:
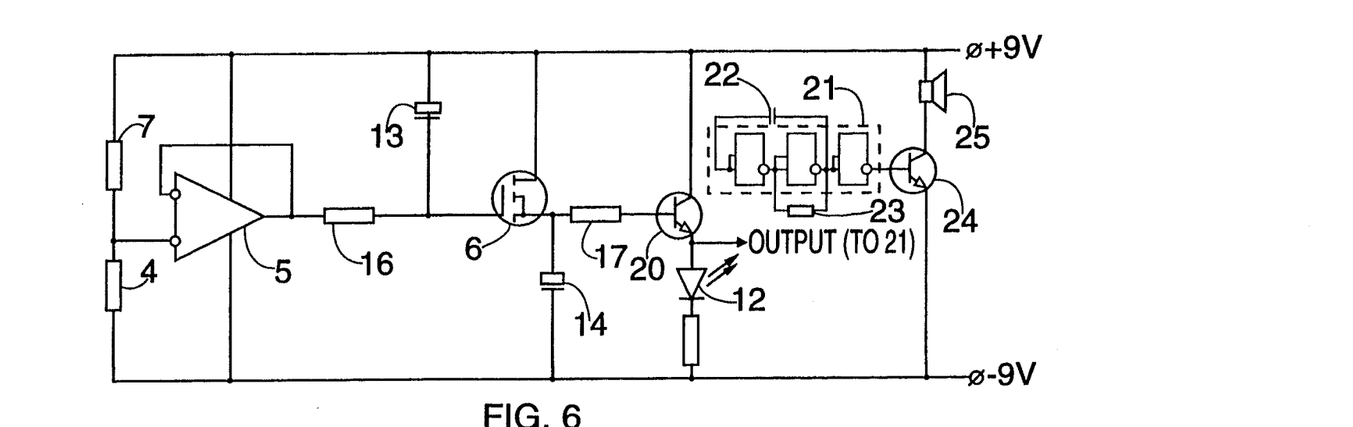

FIGS. 4, 5, and 6 describe possible signal processing circuits diagrams of the smoke-detector made in accordance with the present invention. Such circuits may be used for fire alarm systems and will be referred to as the "Signal Processing Circuits".

FIG. 4 demonstrates the circuit functioning principle. In a smoky medium formed as the result of combustion, the resistance of the smoke-sensitive element 4, formed of the bismuth oxide made in accordance with the present invention, decreases, leading to the change of the potential at the noninverting input of the operational amplifier 5, thus changing the output voltage of the amplifier. The output voltage increase opens the transistor 6 connected to the gate through the resistor 16. As a result, the potential of the control electrode of the thyristor 8 connected with the transistor 6 through the resistor 17 and the timing resistor 11 also increases. Upon achieving the threshold value of the potential at the control electrode of the thyristor 8, the latter opens and the winding of the relay 9 appears under voltage. As a result, the normally closed contacts of the relay 9 open and close the alarm circuit 10.

Reliable functioning of the operational amplifier is due to an application of a mode where the amplification coefficient is equal to one. It is provided by connecting with a short current circuit the inverting input to the operational amplifier output; in this case the detector noise immunity is considerably intensified and its screening becomes unnecessary.

The thyristor 8 operation threshold is set with the help of the trimmer resistor 11. The thyristor 8 opens and switches on the light emitting diode (LED) 12 indicating the detector operation.

The capacitor 13 prevents noise-induced operation, and the capacitor 14 provides smooth switching of the thyristor.

The resistors 7, 15, 16 and 17 serve to set the operation mode of the transistor 6, which is used to match the output of the amplifier 5 and to set the switching threshold of the thyristor 8, respectively.

It is also possible to use another embodiment of the present invention where the thyristor 8, FIG. 4, is substituted for a transistor. In this case, if the smoke does not make contact with the smoke-sensitive element surface, the detector appears in its initial state corresponding to the waiting mode.

FIG. 5 describes an embodiment of the Signal Processing Circuit of the present invention which may be used in aviation. The difference between the embodiments described in FIG. 4 and FIG. 5 is that after switching the thyristor 8 the capacitor 18 becomes charged and through the resistor 19 the voltage is supplied to the base of the transistor 20 which opens and switches on the relay 9. In this case, normally closed contacts of the relay 9 are opened and the signal is supplied to the corresponding indicator. Simultaneously, the normally closed contacts of the relay 9 open, the thyristor 8 switches off, the capacitor 18 discharges, the transistor 20 closes and switches off the relay. Then the cycle is repeated. This additional chain (shown in FIG. 6) allows the formation of an intermittent signal. Besides, noise-induced operation may be unique or short-lived.

FIG. 6 describes the smoke-detector alarm circuit diagram 10 of FIG. 5 with an autonomous power supply consisting of a 9 volt battery. In FIG. 6, the relay 9 of FIG. 4 is replaced by the sound frequency generator 10 comprised of integrated circuit 21, capacitor 22 and resistor 23. The transistor 24 amplifies the signal supplied to the loudspeaker 25 or to a piezo element.

Because the present invention requires the use of only a small number of electronic elements, see, for example, FIG. 5, the smoke sensitive element is simple to construct and may be constructed so as to occupy only a small volume. In accordance with another embodiment of the present invention, an integrated version of smoke-detector is constructed on the same substrate. In this embodiment all the above-mentioned components in the signal processing circuit and the alarm circuit, as well as the smoke-sensitive element will be supported on the same substrate and constructed by any of the well known methods of microelectronics. In this case, it is possible to construct a fully integrated microcircuit in the same substrate together with the signal processing and alarm circuits as a hybrid integrated circuit or microcircuit. It is possible to have the bismuth oxide (deposited and heat treated) on the whole surface of an electrically insulating material, then covering the part of this film with insulating and protecting layers after making of a pair of contacts to the smoke-sensitive element. The smoke-sensitive element comprises a bismuth oxide film deposited on one surface of an electrically insulating material so as to cover all of the integrated circuit (fully integrated or hybrid) and which after being deposited is again covered by insulating and protecting layers.

Figure 7:
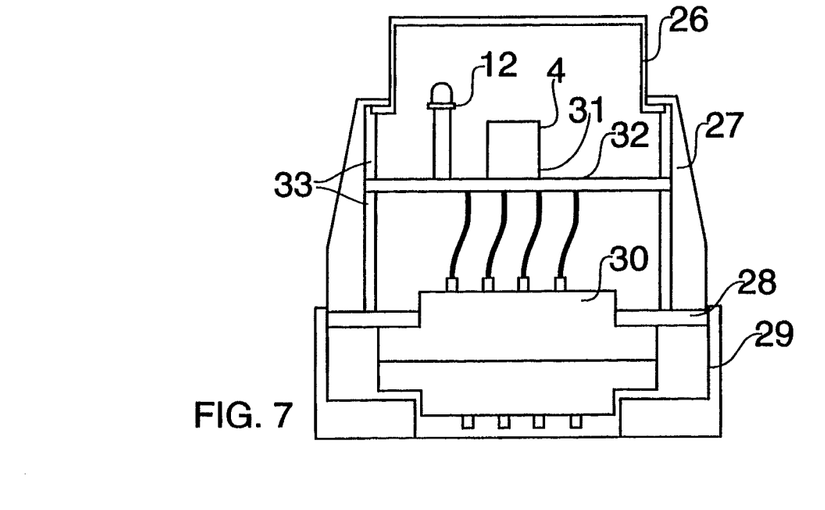
FIG. 7 is a cross-section view of one embodiment of the smoke detector structure of the present invention.

FIG. 7 describes a cross sectional view of one embodiment of a smoke sensor made in accordance with the present invention. This sensor is comprised of several structural frame sections 27, 28, 29, and 33, which can be made of different materials. Section 26 is preferably made from wire cloth to provide for smoke penetration and protecting of sensitive element 4 against mechanical damage. Section 31 provides some support (base) for the smoke-sensitive element 4. Section 32 is the plate on which the electronic circuit is assembled. Plate 32 is positionally fixed with respect to the smoke sensor with the help of ring 33. 12 is a light emitting diode.

Figure 8A:
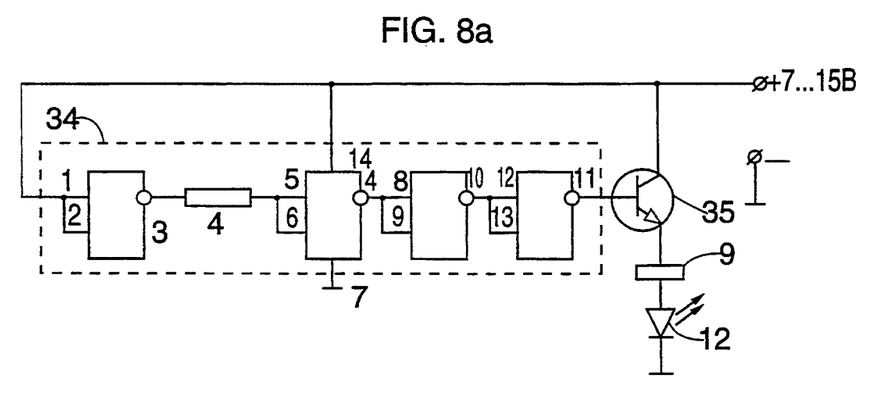
FIGS. 8a and 8b show a signal processing circuit diagram of another preferred embodiment of the present invention.
Figure 8B:
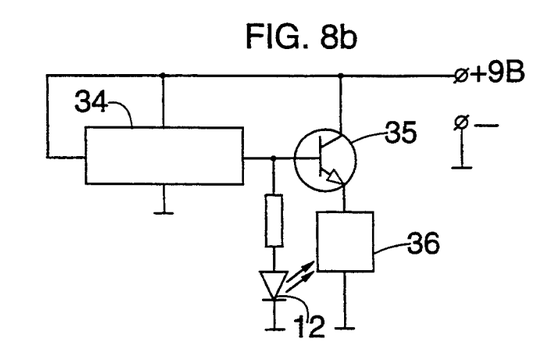

FIGS. 8a and 8b describe another, new embodiment of the signal processing circuit of the smoke-detector made in accordance with the present invention and referred to as the Modern Signal Processing Circuit. This circuit considerably improves the characteristics of the smoke-detecting system by decreasing by many times the power and current consumed in the waiting mode, increasing noise immunity and speed of response, considerably simplifying the diagram, and diminishing the proposed smoke-detector's size and weight.

The parameters of this new preferred embodiment of smoke-detector using the Modern Signal Processing Circuit of the present invention are:

| | |
|---|---|
| Threshold of sensitivity (% of smoke in air) | ≈6% to 7% |
| Coverage | ≦480 cubic meters |
| Current consumption in the waiting mode | 2 nanoamperes |
| Current consumption in the operating (alarm) mode | 30 milliamperes |
| Power consumption in the waiting mode | 0.018 milliwatts |
| Power consumption in the alarm mode | 0.1 watts |
| Working Temperature range (°C.) | −30 to +60° C. |
| Operational relative humidity range, at 27° C. in the absence of condensation and without the need for a heating element | ≦100% |
| Permitted degree of background illumination | unlimited |
| Nominal voltage | 7-15 volts |
| Time of response | <1 second |
| Weight | 40 grams |
| Size | diameter = 55 millimeters height = 25 millimeters |

The main part of the proposed processing circuit is microcircuit 34, made by complementary metal-oxide-semiconductor (CMOS) technology and including 4 logic cells (elements) NOT-AND (NAND) or OR-AND with two inputs each. The state of the output for the first from the left logic cell is a logic zero (0) state. For what is believed to be the first time in the literature, we connect the first logic cell's output with the input of the second logic cell via the smoke-sensitive element made in accordance with the present invention. The second cell is in the logic one (1) state.

As the smoke-sensitive element's resistance is higher than the input resistance of the second logic cell a voltage drop across the smoke-sensitive element in the waiting mode is higher than a drop across the input of the logic cell. Therefore, the output of the second logic cell is in the logic zero (0) state.

The resistance of the smoke-sensitive element considerably decreases in smoky medium which leads to voltage drop redistribution. In the presence of smoke, the voltage drop at the input of the logic cell is greater than that across the smoke-sensitive element and the output of the second cell is now in the logic one (1) state.

The signal undergoes through buffer stages a part (role) of which constitute third and fourth logic cells and feeds into the base of the transistor 35 which switches on the relay 9 or the alarm annuciator 36.

Power in the present invention signal processing circuits is supplied from a constant-voltage source (from 7 to 15 V) which allows the use of the circuit both in centralizated fire systems with a large number of the smoke detectors in the line and for individual consumers with use of an autonomous power supply like a battery.

Although preferred embodiments of the present invention have been described above in detail, it is desired

REFERENCES

Aroutiounian, V. M., Microelectronics technologies-main road for fabrication of solid-state chemical sensors, *Sov. Microelectonics*, vol. 20, No. 4, pp. 337–355, July 1991.

Chorwitz, P. & Hill W., *Skill of Circuit Engineering* (1983, Moscow Mir PH), vol. 1 (in Russian).

Fire Safety, *Explosion Safety* (Baratov, A. N., ed.) (1987, Moscow Chemistry P.H., p. 270) (in Russian).

Hykaway, M., Sears, W. M., Frindt, R. F. & Morrison, S. R., The gas-sensing properties of bismuth molybdate evaporate films, *Sensors and Actuators*, vol. 15, No. 1, pp. 105–118, January 1988

Nitta, T. & Terada. J., Multifunctional ceramic sensors: Humidity-gas sensor, temperature-humidity sensor, *IEEE Trans.* ED 29, No. 1, pp. 95–102, January 1982.

Pandeliser, K. A. & Wang, E. Y., Auger electron spectroscopy investigation of degradation effect in GaAs metal-semiconductor solar cells, *J. Appl. Phys.*, vol. 53, No. 1, pp. 720–723, January 1982.

Pogossian, A. S., Abovian, H. V., Avakian, P. B., Mkrtchian, S. H. & Haroutunian V. M., Bismuth ferrites: New Materials for semiconductor gas sensors. *Sensors and Actuators B*, vol. 4, Nos. 1–4, pp. 545–549, 1991.

Wang, E. Y. & Pandeliser, K. A., The effect of chemical surface treatments on non-native ($Bi_2O_3$) GaAs metal-semiconductor solar cells, *J. Appl. Phys.*, vol. 52, No. 7., pp. 4818–4820, July 1981.

We claim:

1. A method of manufacturing a smoke-sensitive element whose resistance varies as a function of concentration of smoke, said method comprising: depositing a film of bismuth oxide onto a substrate layer of an electrically insulating material; heat treating the deposited bismuth oxide film, wherein said heat treatment comprises heating said film in the air by increasing the temperature of said film at the rate of 180°–240° C. per minute until the temperature of said film is about 670°–730° C., holding said film at about this temperature for about 10–20 seconds and then cooling said film at a rate of 180°–240° C. per minute to room temperature; and providing means for electrically connecting such heat treated film to means for measuring resistance.

2. The method according to claim 1 wherein said bismuth oxide film is comprised substantially of bismuth sesquioxide.

3. The method according to claim 2 wherein said substrate layer is one which is used for dielectric insulation in integrated microcircuit fabrication and overlays a surface of semiconductor or semiconductive alloys used for fabrication of these microcircuits.

4. The method according to claim 3 wherein said substrate layer is $SiO_2$ and overlays a surface of Si.

5. The method according to claim 3 wherein said substrate layer is $Si_3N_4$ and overlays a surface of Si.

6. The method according to claim 3 wherein said substrate layer is $SiO_2$ and overlays a surface of GaAs.

7. The method according to claim 3 wherein said substrate layer is $Si_3N_4$ and overlays a surface of GaAs.

8. The method according to claims 3 wherein said substrate layer is $SiO_2$ and overlays a surface of InP.

9. The method according to claim 3 wherein said substrate layer is $Si_3N_4$ and overlays a surface of InP.

10. The method according to claim 1 wherein depositing said film of bismuth oxide onto a substrate layer is performed by electron beam evaporation.

11. The method according to claim 1 wherein depositing said film of bismuth oxide onto a substrate layer is performed by sputtering.

12. The method according to claim 1 wherein depositing said film of bismuth oxide onto a substrate layer is performed by magnetron sputtering.

13. The method according to claim 1 wherein depositing said film of bismuth oxide onto a substrate layer is performed by cathode deposition.

14. The method according to claim 1 wherein depositing said film of bismuth oxide onto a substrate layer is performed by thermal deposition.

15. The method according to claim 1 wherein depositing said film of bismuth oxide onto a substrate layer is performed by ionic deposition.

16. A method of manufacturing a smoke-sensitive element whose resistance varies as a function of concentration of smoke, said method comprising:

a. depositing a film of bismuth oxide comprised substantially of bismuth sesquioxide onto a substrate layer of an electrically insulating material, wherein said depositing is performed by electron beam evaporation at a rate of 500–1000 angstroms per minute, and wherein said substrate layer is one which is used for dielectric insulation in integrated microcircuit fabrication and overlays a surface of semiconductor or semiconductive alloys used for fabrication of these microcircuits;

b. heat treating the deposited bismuth oxide film, wherein said heat treatment comprises heating said film in the air by increasing the temperature of said film at the rate of 180°–240° C. per minute until the temperature of said film is about 670°–730° C., holding said film at about this temperature for about 10–20 seconds, and then cooling said film at a rate of 180°–240° C. per minute to room temperature.

17. The method according claim 16 comprising the further step of depositing a pair of electrodes on the smoke-sensitive element when the temperature of the film and substrate is 300° C. or less.

18. A method of manufacturing a smoke-sensitive element whose resistance varies as a function of concentration of smoke, said method comprising:

a. depositing a film of bismuth oxide comprised substantially of bismuth sesquioxide onto a substrate layer of an electrically insulating material, wherein said depositing is performed by electron beam evaporation at a rate of 500–1000 angstroms per minute using an electron beam at a power of 0.25–0.40 kilowatts in a chamber in which the pressure is about $10^{-3}$ pascal;

and wherein said substrate layer is one which is used for dielectric insulation in integrated microcircuit fabrication and overlays a surface of semiconductor or semiconductive alloys used for fabrication of these microcircuits;

b. heat treating the deposited bismuth oxide film, wherein said heat treatment comprises heating said film in the air by increasing the temperature of said film at the rate of 180°–240° C. per minute until the temperature of said film is about 670°–730° C., holding said film at about this temperature for about 10–20 seconds, and then cooling said film at a rate of 180°–240° C. per minute to room temperature and c. depositing a pair of electrodes on the smoke sensitive element when the temperature of the film and substrate is less than 300° C.

* * * * *